(12) United States Patent
Steuperaert

(10) Patent No.: US 11,017,885 B2
(45) Date of Patent: May 25, 2021

(54) REMOTE MONITORING OF MEDICAL DEVICES

(71) Applicant: CEPHEID, Sunnyvale, CA (US)

(72) Inventor: Jan Steuperaert, Le Faget (FR)

(73) Assignee: Cepheid, Sunnyvale, CA (US)

( * ) Notice: Subject to any disclaimer, the term of this patent is extended or adjusted under 35 U.S.C. 154(b) by 112 days.

(21) Appl. No.: 16/139,933

(22) Filed: Sep. 24, 2018

(65) Prior Publication Data

US 2019/0104039 A1    Apr. 4, 2019

Related U.S. Application Data

(63) Continuation of application No. 13/828,741, filed on Mar. 14, 2013, now abandoned.

(60) Provisional application No. 61/673,612, filed on Jul. 19, 2012.

(51) Int. Cl.
| | |
|---|---|
| *G06F 15/173* | (2006.01) |
| *G16H 10/40* | (2018.01) |
| *H04L 12/26* | (2006.01) |
| *H04L 29/08* | (2006.01) |
| *H04L 29/06* | (2006.01) |
| *G16H 40/67* | (2018.01) |
| *G16H 40/40* | (2018.01) |

(52) U.S. Cl.
CPC ............ *G16H 10/40* (2018.01); *H04L 43/06* (2013.01); *H04L 63/102* (2013.01); *H04L 67/12* (2013.01); *G16H 40/40* (2018.01); *G16H 40/67* (2018.01)

(58) Field of Classification Search
CPC . G06N 3/08; G06N 3/04; G06N 20/00; H04L 67/306; H04W 72/042
See application file for complete search history.

(56) References Cited

U.S. PATENT DOCUMENTS

| | | | |
|---|---|---|---|
| 6,463,417 | B1 | 10/2002 | Schoenberg |
| 2001/0039502 | A1 | 11/2001 | Case |
| 2002/0143961 | A1 | 10/2002 | Siegel |
| 2003/0212379 | A1* | 11/2003 | Bylund .............. A61B 5/14514 604/504 |
| 2008/0046484 | A1 | 2/2008 | Ellis |

(Continued)

FOREIGN PATENT DOCUMENTS

WO    2010132617 A2    11/2010

OTHER PUBLICATIONS

Liu, Naifeng, "Rules for construction and management of Information Department," Southeast University Press, Dec. 2005, pp. 119-121.

(Continued)

*Primary Examiner* — Brian Whipple
*Assistant Examiner* — Gregory P Tolchinsky
(74) *Attorney, Agent, or Firm* — Kilpatrick Townsend & Stockton LLP

(57) ABSTRACT

A remote monitoring system for medical data collection can include a data-flagging process embeds authorization and settings information into a file containing the test results. Such data flagging can occur at a medical device or testing site, and may be based in policy settings received from a remote system. A file containing the test results can also include data category information that can be used to protect sensitive information by preventing such information from being communicated to the wrong server.

20 Claims, 10 Drawing Sheets

(56) References Cited

U.S. PATENT DOCUMENTS

| | | |
|---|---|---|
| 2008/0104104 A1 | 5/2008 | Nolan |
| 2008/0262561 A1* | 10/2008 | Catto .................. A61N 1/37247 607/30 |
| 2009/0171694 A1 | 7/2009 | Ross |
| 2010/0292556 A1 | 11/2010 | Golden |
| 2011/0148624 A1* | 6/2011 | Eaton ....................... H04L 67/12 340/539.13 |
| 2013/0066644 A1* | 3/2013 | Dicks ................... A61B 5/0022 705/2 |
| 2013/0102853 A1* | 4/2013 | Halvorson .......... G06F 19/3418 600/300 |

OTHER PUBLICATIONS

Steele et al., "HealthPass: Fine-grained Access Control to Portable Personal Health Records," 24$^{th}$ IEEE International Conference on Advanced Information Networking and Applications, Apr. 20, 2010, 1012-1019.

* cited by examiner

Reporting policy settings: Institute01

| Reporting Group Name: | Activate ☑ | Allow systems from my institution to enable this reporting group | |
|---|---|---|---|
| Institute01 | Public ☑ | Allow systems from certain countries to enable this reporting group | Edit countries... |

| | | Allow user | Force on | Force off |
|---|---|---|---|---|
| Basic | Reports which test was done, version, test type. | ○ | ● | ○ |
| Assay Info | Report lot number, cartridge ID, Sample type, test duration. | ○ | ○ | ● |
| Details | Reports control details about the assay | ○ | ○ | ● |
| Support | Reports technical details about the assay (large data!) | ● | ○ | ○ |
| System User | Reports who the user is | ○ | ● | ○ |
| Test Results | Reports the diagnostic result | ○ | ● | ○ |

Edit Reagents...   Cancel   Save

```xml
<?xml version="1.0" encoding ="UTF-8" standalone="no"?>
<CephReporting>
    <Policy>
        <PolicyID>0123456</PolicyID>
        <Name>Institute01</Name>
        <Allowed>true</Allowed>
        <AsOfDate>2011/01/01 00:00:00.0001</AsOfDate>
        <TestsPerCycle>5</TestsPerCycle>
    </Policy>
    <Assays>
        <Assay>Xpert MTB/Rif</Assay>
    </Assays>
    <Instructions>
        <Instruction name="Basic">YES</Instruction>
        <Instruction name="Assay">YES</Instruction>
        <Instruction name="Result">YES</Instruction>
        <Instruction name="Details">NO</Instruction>
        <Instruction name="Support">NO</Instruction>
        <Instruction name="SystUser">ALLOW</Instruction>
    </Instructions>
    <TransientInstructions>
        <Instruction name="Resend">YES</Instruction>
    </TransientInstructions>
</CephReporting>
```

```xml
<?xml version="1.0" encoding ="UTF-8" standalone="no"?>
<CephTest>
    <Policies>
        <Policy>
            <PolicyID>0123456</PolicyID>
            <Name>Institute01</Name>
            <Authorize name="Basic"/>
            <Authorize name="Assay"/>
            <Authorize name="Result"/>
            <Authorize name="SystUser"/>
        </Policy>
        <Policy>
            <PolicyID>5423456</PolicyID>
            <Name>WHO</Name>
            <Authorize name="Basic"/>
            <Authorize name="Result"/>
        </Policy>
    </Policies>
    <Test>
        <ID>
            <ExportDate>2012-02-16</ExportDate>
            <Model>GX</Model>
            <SystemSN>0004567890</SystemSN>
            <ModuleSN>0034567890</ModuleSN>
            <StartDate>2011/02/28 14:29:47.421</StartDate>
            <GUID>F089E2FFD80B4340A434B18BBF10D764</GUID>
            <ErrorDetail>Done-</ErrorDetail>
        </ID>
        <Basic>
            <AssayName>Xpert MTB/Rif</AssayName>
            <AssayVersion>4</AssayVersion>
            <TestType>QC</TestType>
        </Basic>
        <Assay>
            <Lot>00152</Lot>
            <CartridgeSN>1234567890</CartridgeSN>
            <SampleType>Swab</SampleType>
            <ModuleName>B3</ModuleName>
            <SoftwareVersion>6.0</SoftwareVersion>
            <EndDate>2011/02/28 15:18:32.124</EndDate>
        </Assay>
        <Result>NEGATIVE</Result>
        <SystUser>
            <AccountName>BradC</AccountName>
        </SystUser>
    </Test>
</CephTest>
```

600

FIG. 6

REMOTE MONITORING OF MEDICAL DEVICES

CROSS-REFERENCES TO RELATED APPLICATIONS

This application is a continuation of U.S. application Ser. No. 13/828,741, filed Mar. 14, 2013 which claims benefit under 35 USC 119(e) of U.S. Provisional Application No. 61/673,612, filed on Jul. 19, 2012, both of which are incorporated by reference herein for all purposes.

BACKGROUND

Medical data collection can involve remotely monitoring a distributed network of medical devices, such as molecular diagnostic systems and/or other testing devices, and aggregating and processing the data provided by these medical devices into useable information. Because the medical devices may be located throughout the world, the information can be used by a host of entities, such as governments, hospitals, and other institutions to not only monitor the status of individual medical devices, but also to decipher large-scale epidemiological data and determine other valuable health and disease information. Current aggregation and processing of data from such medical data collection, i.e., sifting through data as it trickles in from the medical devices, can be restrictive. And because different entities (institutions and individuals) want to view different types of data from the medical devices, it can be difficult to provide personalized reporting data to a requesting entity in a quick manner (e.g., in real time).

BRIEF SUMMARY

Embodiments of the current invention provide for a remote monitoring system for medical data collection that includes a data-flagging process that embeds authorization and settings information into a file containing the test results. Such data flagging can occur at a medical device or testing site, and may be based in policy settings received from a remote system. A file containing the test results can also include data category information that can be used to protect sensitive information by preventing such information from being communicated to the wrong server.

In some embodiments, a computer-implemented method for processing test results of a medical device, according to the disclosure, can comprise receiving, via a communication interface, settings information indicative of one or more authorization levels associated with an entity. Each of the one or more authorization levels is indicative of a type of data, from the test results of the medical device, to include in reporting information. The method can further comprise obtaining the test results from the medical device, and creating, with a processor, a file comprising the reporting information. The reporting information can comprise information indicative of the entity, the one or more authorization levels associated with the entity, and at least a portion of the test results. The method can also comprise sending the file via the communication interface.

In some embodiments, the method optionally can comprise one or more of the following features. The method can comprise providing a user with an interface configured to receive an input, and adjusting at least one of the one or more authorization levels based, at least in part, on the input. The method can comprise adjusting, based on the settings information, at least one of the following exemplary settings of the medical device: a number of tests reported in a certain period of time, a type of test to include in the reporting information, or a starting date to provide the reporting information. Additional settings that may be included and adjusted will be well known to persons of ordinary skill in the art. The at least the portion of the test results can comprise a first data set associated with a first authorization level, and a second data set associated with a second authorization level. Additional data sets and authorization levels can also be included. Receiving the settings information can comprise scanning a particular data location for the settings information. Sending the reporting information can comprise storing the reporting information in a particular data location for transmittal. The method can comprise formatting the reporting information in a meta-language. The reporting information can also comprise an identifier of the medical device. Creating the file can also comprise including, in the reporting information, a cartridge identifier related to the at least the portion of the test results and/or data category information related to at least a portion of the reporting information.

In some embodiments, a computer-readable storage medium, according to the disclosure, has computer-executable instructions embedded thereon for processing test results of a medical device. The computer-readable storage medium can comprise instructions for receiving settings information indicative of one or more authorization levels associated with an entity. Each of the one or more authorization levels is indicative of a type of data, from the test results of the medical device, to include in reporting information. The computer-readable storage medium can also comprise instructions for obtaining the test results from the medical device, and creating a file comprising the reporting information. The reporting information can comprise information indicative of the entity, the one or more authorization levels associated with the entity, and at least a portion of the test results. The computer-readable storage medium further includes instructions for sending the file via the communication interface.

In some embodiments, the computer-readable storage medium optionally can comprise one or more of the following features. The computer-readable storage medium can include instructions for providing a user interface configured to receive an input, and adjusting at least one of the one or more authorization levels based, at least in part, on the input. The computer-readable storage medium can comprise instructions for adjusting, based on the settings information, at least one of the following settings of the medical device: a number of tests reported in a certain period of time, a type of test to include in the reporting information, or a starting date to provide the reporting information. Additional settings that may be included and adjusted will be well known to persons of ordinary skill in the art. The computer-readable storage medium can comprise instructions for formatting the reporting information such that a first data set of the at least the portion of the test results is associated with a first authorization level, and a second data set of the at least the portion of the test results is associated with a second authorization level. Additional data sets and authorization levels can also be included. The instructions for sending the reporting information can comprise instructions for storing the reporting information in a particular data location for transmittal. The computer-readable storage medium can include instructions for formatting the reporting information in a meta-language. The computer-readable storage medium can comprise instructions for including, in the reporting information, an identifier of the medical device and/or a cartridge identifier related to the at least the portion of the test results. The instructions for creating the file further can comprise instructions for including, in the reporting information, data category information related to at least a portion of the reporting information.

In some embodiments, a computer-implemented method for reporting test results from a medical device, according to the description, can comprise receiving, via a communication interface, reporting information indicative of the test results from the medical device. The reporting information can comprise information indicative of an entity, one or more authorization levels associated with the entity, where each of the one or more authorization levels is indicative of a type of data from the test results of the medical device, and at least a portion of the test results. The method further can comprise receiving a request to report the test results, where the request associated with the entity, and determining, with a processor, a subset of the at least the portion of the test results to report based, at least in part, on the one or more authorization levels and the entity. The method can also comprise providing a report based, at least in part, on the subset.

In some embodiments, the method optionally can comprise one or more of the following features. The report can be provided via a web-based portal. The reporting information can further comprise an identifier of the medical device, and the method can further comprise determining a location associated with the medical device based, at least in part, on the identifier, and providing an indication of the location in the report. The method can include sending, via the communication interface, settings information indicative of the one or more authorization levels associated with the entity. The report can be based, at least in part, on test results from a plurality of medical devices.

In some embodiments, a system for reporting medical test results, according to the description, can comprise a first server configured to send settings information indicative of one or more authorization levels associated with an entity, and at least one medical device. The at least one medical device is configured to receive the settings information create reporting information regarding test results of a test conducted by the at least one medical device. Creating the reporting information can comprise embedding the reporting information with information indicative of the entity, the one or more authorization levels associated with the entity, and at least a portion of the test results. The at least one medical device further is configured to send the reporting information. The system can also comprise at least a second server configured to receive the reporting information from the at least one medical device, and receive a request to report the test results of the at least one medical device, where the request associated with the entity. The at least second server further is configured to determine a subset of the at least the portion of the test results to report, based on the reporting information, and provide a report based, at least in part, on the subset.

In some embodiments, the system optionally can comprise one or more of the following features. The report can be provided via a web-based portal. The at least one medical device can be configured to comprise, in the reporting information, an identifier of the at least one medical device, and the at least second server can be further configured to determine a location associated with each of the at least one medical device, at least in part, on the identifier, and provide an indication of the location in the report. The at least second server can be the same server as the first server. The first server can be configured to send settings information regarding at least one of the following settings of the at least one medical device: a number of tests reported in a certain period of time, a type of test to include in the reporting information, or a starting date to provide the reporting information.

Numerous benefits are achieved by way of the present invention over conventional techniques. For example, data-flagging test results with authorization settings can allow for reliable, real-time data filtering based on the authorization type of an entity attempting to view the reporting results. The reporting results can be shown using geographical maps and/or other techniques to show up-to-date test result information that can enable an entity to quickly react to infectious outbreaks or other medical phenomena. These and other embodiments of the invention, along with many of its advantages and features, are described in more detail in conjunction with the text below and attached figures.

BRIEF DESCRIPTION OF THE DRAWINGS

A further understanding of the nature and advantages of various embodiments may be realized by reference to the following figures. In the appended figures, similar components or features may have the same reference label.

FIG. 3 is an exemplary illustration of a reporting policies user interface, providing an example of how a viewing entity can be granted certain authorization levels.

FIG. 4 illustrates the content of a reporting policies file, corresponding to the exemplary reporting policies shown in FIG. 3.

FIG. 5 is an exemplary illustration of a local reporting settings user interface, providing an example of how a lab user can implement the reporting policies from a reporting policies file.

FIG. 6 illustrates the content of a reporting file, corresponding to the exemplary reporting policies shown in FIGS. 3-5.

DETAILED DESCRIPTION

Some embodiments of the current invention provide for a remote monitoring system for medical data collection that includes a data-flagging process in which authorization and settings information can be embedded into a file containing the test results. Such data flagging can allow for reliable, real-time data filtering based on the authorization type of an entity attempting to view the reporting results (hereafter "viewing entity"). Although embodiments provided herein relate to the gathering and processing of medical data, such as medical test results, the features and techniques disclosed can be extended to other distributed networks where levels of authorization are utilized to access different amounts and/or types of data collected by the network.

Figure 1A:
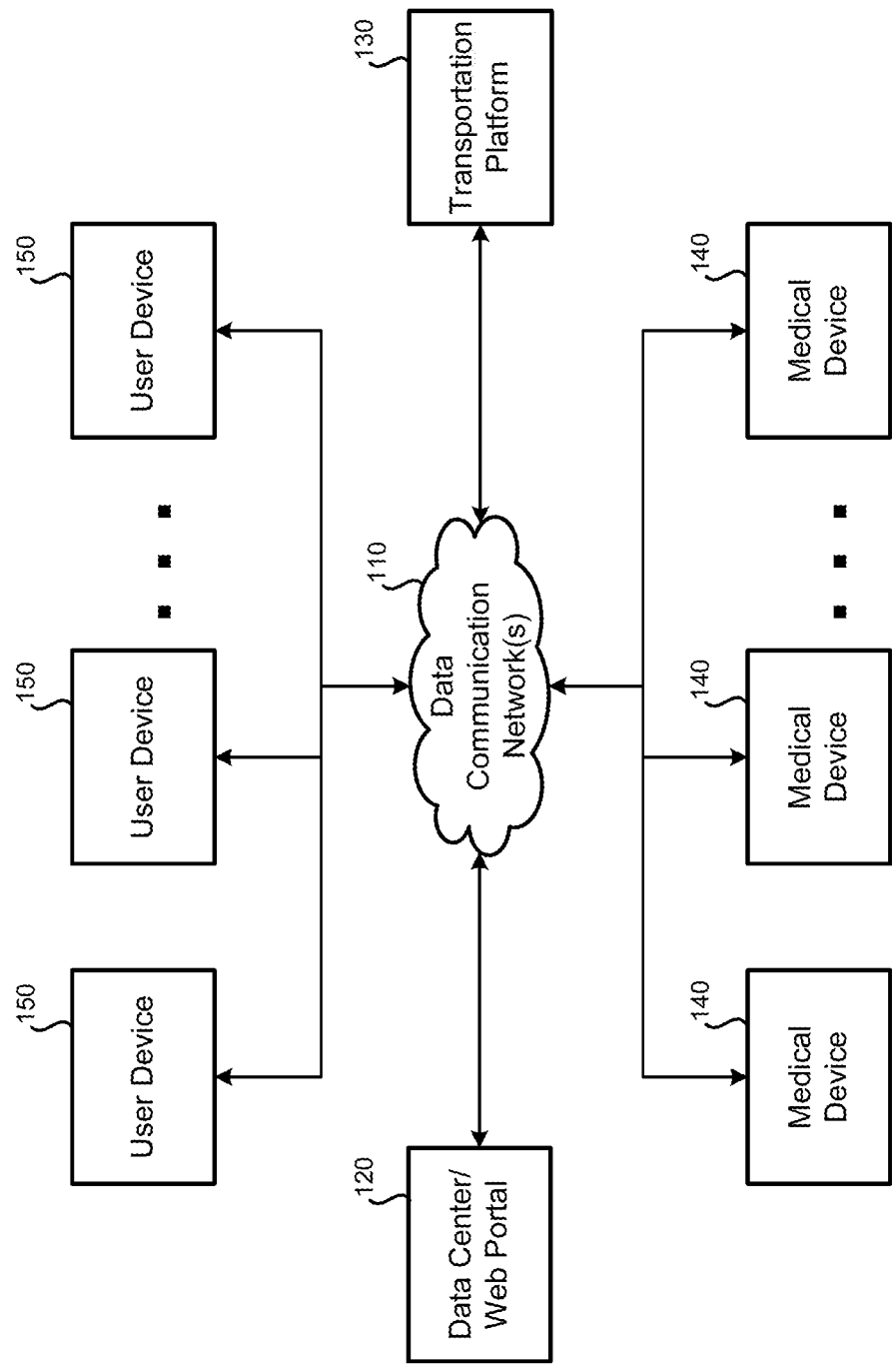
FIGS. 1A and 1B are simplified block diagrams showing two example configurations of a distributed network capable of performing the data-flagging processes described herein.
Figure 1B:
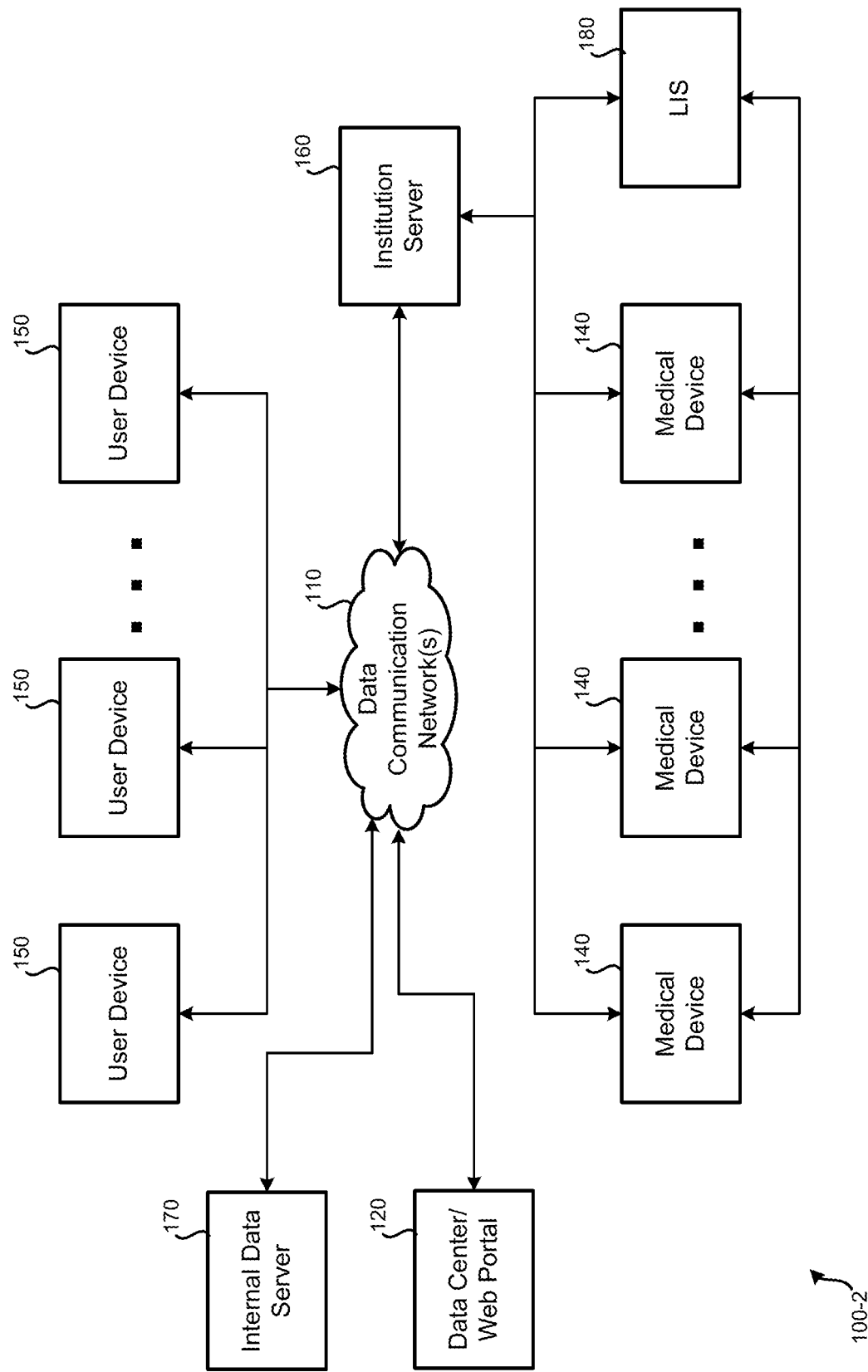

FIGS. 1A and 1B are simplified block diagrams showing two example configurations of a distributed network 100 capable of performing the data-flagging processes described herein. Some embodiments may differ from the examples shown. For example, some embodiments can combine, separate, add to, and/or omit components shown in FIGS. 1A and 1B. Furthermore, the functionality of each of the components can be provided by one or more devices (e.g., computing devices) disposed in one or more geographical locations.

A first distributed network 100-1 is shown in FIG. 1A. In this embodiment, the first distributed network 100-1 includes one or more medical devices 140, a transportation platform 130, a data center/web portal 120, one or more user devices 150, and data communication network(s) 110 communicatively coupling these components together. Medical data is provided by the one or more medical devices 140. As described in more detail below, medical devices 140, such as molecular diagnostic systems, can comprise a combination of testing and computing components configured to gather data from and/or conduct medical tests. The one or more medical devices 140 can be located at various different geographic locations to help provide large-scale epidemiological data and determine other valuable health and disease information among one or more populations.

The transportation platform 130 can facilitate the transportation of data between the data center/web portal 120 and the one or more medical devices 140. It can include components (e.g., software) installed on the one or more medical devices 140 and/or utilized by the data center/web portal 120, as well as components (e.g., software and/or hardware) for data storage and/or processing functionality. With these capabilities, the transportation platform 130 can deliver data between the one or more medical devices 140 and the data center/web portal 120 in a secure and automated manner, providing any needed formatting and/or other changes to the data being transported. In some embodiments, the transportation platform 130 can further include diagnostic services such as monitoring parameters collected on the one or more medical devices 140, generating corresponding alerts, and interacting with the one or more medical devices 140 by sending files, by desktop sharing, and/or by upgrading software.

The data center/web portal 120 can aggregate and process medical data and provide a viewing entity with the processed medical data in various forms (e.g., lists, graphs, geographic maps, and the like) in accordance with the viewing entity's level of authorization. Furthermore, the data center/web portal 120, which can include one or more centralized or distributed computer systems (e.g., computer servers), can also provide an institution administrator with an interface to enable the institution administrator to set one or more reporting policies that can determine the authorization levels associated with the medical data. The data center/web portal 120 can provide a web-based portal and/or other user interface to enable the viewing entities and/or institution administrator to communicate with the data center/web portal 120 using one or more user devices 150. The one or more user devices 150 can include any of a variety of devices, such as a computer terminal, personal computer, tablet, smart phone, and the like. Depending on desired functionality, the one or more user devices 150 can communicate with the data center/web portal 120 via an Internet browser and/or specialized software application executed on the one or more user devices 150. Different components of the data center/web portal 120 may execute different tasks. In some embodiments, a first server can be utilized to set reporting policies, while a second, third, or more server(s) can be utilized to provide a report of test results. In some embodiments, both tasks can be performed on a single server (or other computer system).

The data communication network(s) 110 enables communication between other components of the distributed network 100. The data communication network(s) 110 can comprise any combination of a variety of data communication systems, for example, cable, satellite, wireless/cellular, or Internet systems, or the like, utilizing various technologies and/or protocols, such as radio frequency (RF), optical, satellite, coaxial cable, Ethernet, cellular, twisted pair, other wired and wireless technologies, and the like. The data communication network(s) 110 can comprise packet- and/or circuit-type switching, and can include one or more open, closed, public, and/or private networks, including the Internet, depending on desired functionality, cost, security, and other factors.

With these components, the distributed network 100 can implement a data-flagging process that merges authorization and settings information into a file containing the test results. Reliable, real-time data filtering based on the authorization type of a viewing entity can then be performed on the test results to provide responsive reporting. This data-flagging process begins when an institution administrator (e.g., an authorized user from a hospital, doctor's office, university, or other institution that owns and/or operates the medical devices 140) defines the one or more reporting policies for certain test results. In some embodiments, an institution administrator can utilize a user device 150 to access a web-based portal and indicate reporting policies that determine which tests are reported, how often the tests are reported, the effective dates to implement the reporting (e.g., a starting date to start the reporting), and more. Reporting policies can also define which viewing entities may access the reporting results, and a level of authorization each viewing entity will have. In some exemplary embodiments, an institution administrator can create reporting policies to grant a viewing entity, such as the World Health Organization (WHO) one or more levels of authorization to review certain test results. These levels of authorization determine the types of data reported to the viewing entity (e.g., WHO).

Once the reporting policies are finalized, they can be packaged in a reporting policies file (e.g., an XML file) and distributed to one or more of the institution's medical devices 140 in the distributed network 100. (The reporting policies file may identify the medical devices 140 to which the reporting policies file is to be distributed.) The recipient medical devices 140 can process the reporting policies file and implement the reporting policies accordingly. When medical tests are completed, the medical devices 140 can include the test results in one or more test result files, which are transmitted by the transportation platform 130 to the data center/web portal 120 according to the reporting policies. The test result files can be "flagged," or embedded, with information regarding the authorization levels of reports for each viewing entity. With the authorization included with the test results in a single file in this manner, the data center/web portal 120 can manipulate the data for each viewing entity in real time with little additional processing via, for example, a web-based portal.

The data provided to the viewing entity can vary, depending on, among other things, authorization levels. The distributed network 100 can include medical devices 140 from multiple institutions, allowing a viewing entity to receive aggregate data from different institutions. The data center/ web portal 120 also be configured to provide the location of medical devices 140 on a map, and may allow a lab user, the institution administrator, and/or another authorized user to associate a particular medical device 140 with a specific location. The map not only can indicate the location of medical devices 140, but can also indicate corresponding test results for those medical devices 140.

Embodiments of a distributed network 100 of may provide the functionality described herein independent of other systems. Nonetheless, some embodiments may incorporate and/or be used in conjunction with other systems, such as a Laboratory Information System (LIS) (also known as a Laboratory Management System or Laboratory Information Management System). In so doing, some embodiments can, in addition to providing the functionality described herein, provide sample tracking and management, assay data management, data mining, data analysis, electronic laboratory notebook (ELN), and other functions, depending on desired functionality.

The second distributed network 100-2 shown in FIG. 1B illustrates an embodiment of a distributed network 100 having an LIS incorporated therein. The second distributed network 100-2 of FIG. 1B has many of the same components as the first distributed network 100-1 of FIG. 1A, which can provide the same and/or similar functionality as described above in relation to FIG. 1A. The second distributed network 100-2, however, also includes an LIS 180 communicatively coupled with the medical devices 140, thereby enabling the second distributed network 100-2 to receive data from and/or provide data to the LIS 180 of one or more institutions.

An institution server 160, which may be provided and/or maintained by an institution, is also connected with the medical devices 140 and LIS 180. The institution server 160 can be communicatively coupled with the medical devices 140 and/or LIS 180 via, for example, a private local area network (LAN) and/or wide area network (WAN). The transportation functionality of the transportation platform 130 of FIG. 1A can also be provided, in whole or in part, by the institution server 160. Some embodiments can utilize both an institution server 160 and a transportation platform 130. Additionally, the institution server 160 can monitor all medical devices 140 of a particular institution, aggregate and report medical device data for reporting to the institution, and/or report medical device data to the data center/ web portal 120. Although only one institution server 160 is shown, many institution servers 160 may exist in a distributed network 100 in which test results for medical devices 140 of many institutions are processed.

An internal data server 170 can be maintained by a service provider of the second distributed network 100-2, enabling the service provider to communicate with the medical devices 140, data center/web portal 120, and/or other components of the second distributed network 100-2 to manage devices, access rights, and more. In some embodiments, the internal data server 170 can, along with the institution server 160 and data center/web portal 120, collect and maintain data from medical devices 140 for analysis and/or integration with other applications.

In the second distributed network 100-2, data from test results of the medical devices 140 can be relayed from the institution server 160 to the data center/web portal 120, and from the data center/web portal 120 to the internal data server 170. The content of the data communicated at each of these stages can vary, and may be governed by relevant governmental regulations. For example, an institution server 160 may maintain patient data corresponding to particular test results that is not relayed to the data center/web portal 120 or internal data server 170 in order to comply with, for example, the Health Insurance Portability and Accountability Act (HIPAA) Privacy Rule and/or other such regulations.

To help ensure that a system does not receive information it should not be able to access, the institution server 160, data center/web portal 120, and/or internal data server 170 can implement server protection policies to help prevent the transmittal of certain data. These server protection policies can be defined by institution administrator and stored by the institution server 160, which relays the server protection policies to the other systems.

In some embodiments, the server protection policies can be implemented in a two-phase communication protocol between child system (i.e. a system sending test result information) and parent system (i.e., a system receiving the test result information). First, the child system sends an initiation message to the parent system containing the data category and the owner of the dataset to come next, in addition to child system and message identifiers. The parent system sends a response message back to accept or reject the initiation message, depending on the owner, data category information, and the parent system's own server protection settings. If the parent system accepts the initiation message, the child system will send the dataset. But if the parent system rejects the initiation message, the child system will not send the dataset, thereby preventing the parent system from ever receiving information it should not have access to, according to server protection policies.

The data categories used in the server protection policies can vary, depending on implementation. Administrators can define and/or specify which data categories are allowed inbound from specific owners. Moreover, the server protection policies can be configured to allow data from certain data categories to be sent by particular systems. For example, patient data may be communicated from the institution server 160 to the internal data server 170 in instances where both are maintained by the same entity.

In some embodiments, distributed networks 100 can vary from those shown in FIGS. 1A and 1B. For example, additional medical devices 140, institution servers 160, data center/web portals 120, and/or internal data servers 170 can be added. For example, multiple data center/web portals 120 can be utilized to report to different agencies (e.g., WHO, GMO, etc.). Additional systems can be "daisy chained" to add additional reporting layers, and each layer can be configured with different settings as to what is reported and to which level of detail. In some embodiments, the systems of the distributed networks 100 can be configured to report data to multiple other systems (i.e., a child system can report to multiple parent systems). The data sent and corresponding server protection policies can vary for each parent/child relationship. For example, a medical device can send disease results to the institution server 160 and report technical issues directly to the data center/web portal 120.

Figure 2:
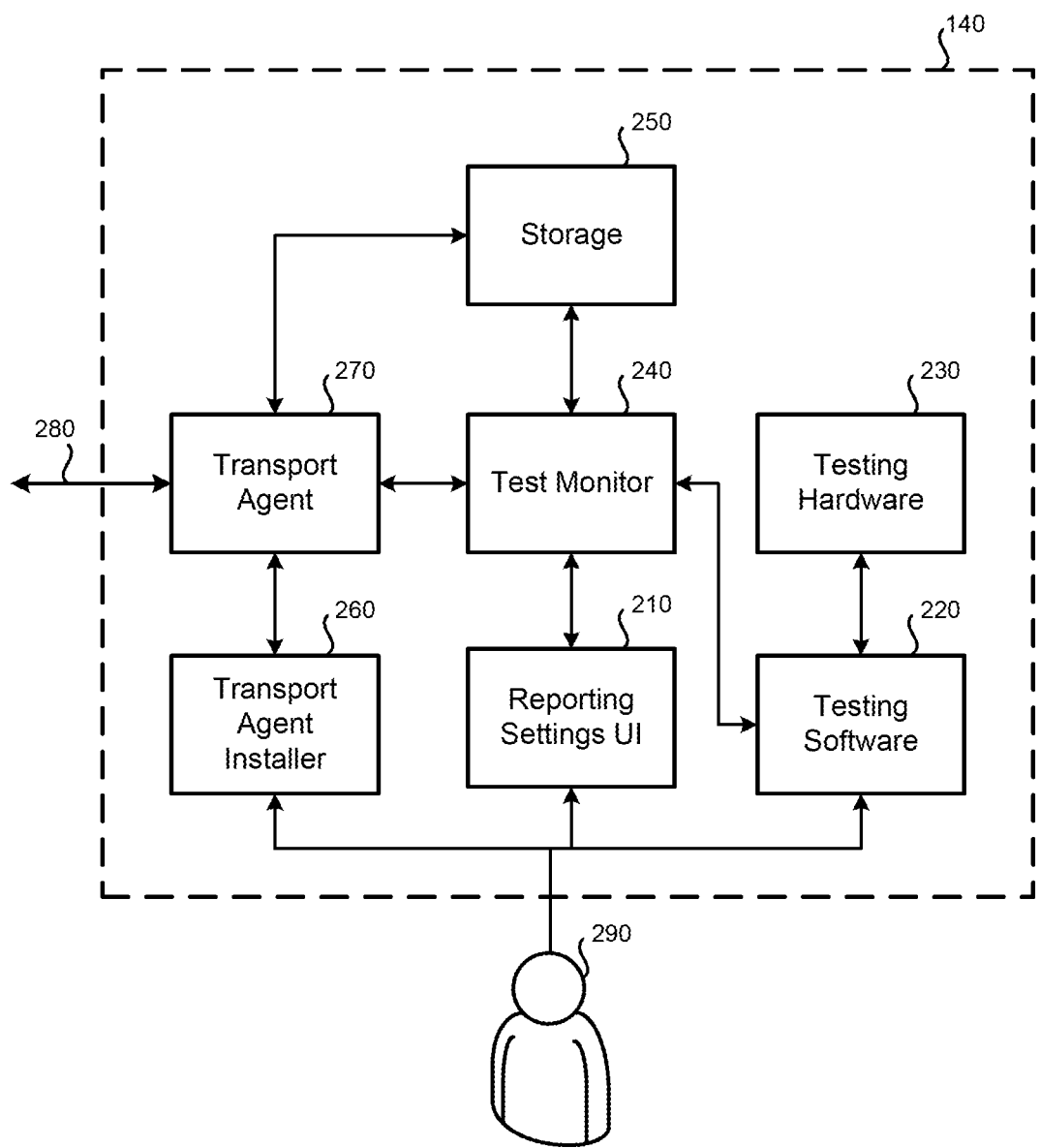
FIG. 2 is a simplified block diagram that illustrates various components of a medical device configured to provide flagged test results (or other medical data).

FIG. 2 is a simplified block diagram that illustrates various components of a medical device 140 configured to provide flagged test results (or other medical data). Components can be implemented, for example, using a combination of software and hardware, which can be incorporated into a computer system (such as that described in relation to FIG. 9). As with other embodiments provided herein, the medical device 140 shown in FIG. 2 is provided as a non-limiting exemplary embodiment. Various embodiments can combine, separate, add, and/or omit various components. For example, some embodiments can omit the transport agent installer 260 and perform similar functionality through other modules and/or means. A person of ordinary skill in the art will recognize various modifications that fall within the scope of the present invention.

Transport agent installer 260 and transport agent 270 are components of the medical device 140 that enable the medical device 140 to utilize the transportation platform 130. The transport agent installer 260 can help ensure proper setup between the medical device 140 and the transportation platform 130. Upon setup, a lab user 290 (or other user of the medical device) can provide the reporting policies user interface (UI) 210 with address and contact information, as well as device identification information (e.g., model number, serial number, and/or other identifier), which is sent, via communication link 280, to the data center/web portal 120, which can assign the device to an institution and location. In some embodiments, the data center/web portal 120 can be configured to assign the medical device to a specific location automatically, based on location data from a network device (e.g., cell phone tower, wireless access point, etc.) and/or other location information.

A transport agent 270 can receive a reporting policies file that describes the reporting policies of certain test results, and place it in storage 250 for retrieval by the test monitor 240. In some embodiments, for example, the reporting policies file can be placed in a particular data location (e.g., a "policy" folder), that is periodically scanned or otherwise checked by the test monitor 240. Using the reporting policies user interface (UI) 210, the test monitor 240 can then request the lab user 290 to confirm the reporting policies, if applicable, before implementing the policy as a reporting setting on the medical device 140. In some embodiments, depending on functionality and ethical concerns, a reporting policy may impact medical tests carried out by testing hardware 230, in which case the test monitor 240 can communicate with the testing software 220 to ensure that testing is carried out accordingly.

Depending on desired functionality, testing software 220 and/or other components of the medical device 140 can be configured to allow the lab user 290 to append test results with custom data. In some embodiments, the testing software 220 can provide the lab user 290 with a form for entering the appended data, which can be customized to meet a specific institution's needs. The form can indicate the field type, the field label, and the data category of the field (which can be used in the server protection policies previously described). Table 1 provides an example of the data fields for a flu testing form:

TABLE 1

Flu Testing Form

| Label | Type | Data Category |
| --- | --- | --- |
| Decade age | List of ranges | Patient demographics |
| Patient zip code | 10-character string | Patient demographics |
| Cell count (ppm) | Number | Patient result |
| Extra notes | Freeform text | Patient ID |

Here, because freeform text may include a patient name, the data category can include a corresponding indication as a precautionary measure.

When using the testing software 220, the lab user 290 can select a form to use and enter in the corresponding data. The medical device 140 can verify particular custom data received against the data type indicated in the form. If not compliant, the data in the non-complying field can be replaced by an error code so that the situation can be detected. This verification mechanism can allow an institution to design communication directly from new or pre-existing application to the functionality of adding custom data provided by the testing software 220.

Custom data can be applied to test results of the medical device 140 in several ways. For example, the lab user 290 can scan the barcode(s) of a specific assay cartridge(s) or specify a time range for which the data is to be applied to test results. The custom data (e.g., cartridge identifier, lot identifier, etc.) of the form is then appended to and reported with test results of the medical device 140. By enabling custom data to be appended to test results in this manner, this custom data can be linked to specific lots, cartridges, diagnostic results, laboratory location, and more. This can allow for various trend detection in the aggregate data, with better medical value than trending the test result alone would provide. It can also provide for easier error detection where it is determined that certain lots may have been subject to errors, certain cartridges were defective, etc.

Reporting policies can impact various aspects of medical data collection to accommodate various different reporting preferences. In some embodiments, reporting policies can be private or public. Private policies can be propagated to medical devices 140 associated with a particular institution. Public policies can be propagated to medical devices 140 of multiple institutions (e.g., all institutions in a given list of countries). In some embodiments, institution administrators for each of the receiving institutions can be notified of these public reporting policies and can approve them before they are sent to their respective medical devices 140.

Reporting policies can include a variety of other information. In some embodiments for example, policies can determine the type of tests that are reported and included in reporting, how often the tests are repeated (e.g., the number of tests reported in a certain period of time), a starting date to provide the reporting information (which can include information from tests conducted prior to the policy date), categories of test data to report, and the like. Depending on desired functionality, a medical device 140 can provide a lab user 290 with the option to approve, override, and/or change some or all reporting policies before they are implemented in the medical device 140 as reporting settings.

Reporting policies can provide one or more authorization levels to a viewing entity by indicating categories of test data (i.e. data sets) that can be reported to the viewing entity. FIG. 3 is an illustration of a reporting policies user interface 300, providing an example of how a viewing entity can be granted certain authorization levels. In this example, the reporting policies user interface 300, which can be shown on a screen or other electronic display of a user device 150 (e.g., a computer monitor), enables an institution administrator to select various categories of test data to be shown to the viewing entity, or reporting group, named "Institute01." For each category of data (namely, "Basic," "Assay info," "Details," "Support," "System User," and "Test Results"), the institution administrator is given the option to include the category in reporting for Institute01 ("Force on"), exclude the category from reporting for Institute01 ("Force off"), or allow a lab user 290 to decide whether to include a particular category of data ("Allow user").

As indicated above, reporting policies can include a variety of other data. Thus, the reporting policies user interface 300 can include options to adjust other reporting policies. In the example shown in FIG. 3, the reporting policies user interface 300 allows a user to "activate" the reporting policies (i.e., send the reporting policies to medical devices 140 of the institution), make the reporting policies public, edit the list of countries associated with public reporting policies, edit the reagents involved in the medical tests, and save or cancel edits to the reporting policies for the viewing entity. Depending on desired functionality and available reporting policies, embodiments of a reporting policies user interface 300 can include additional and/or alternative options for defining and/or adjusting reporting policies.

FIG. 4 illustrates the content 400 of a reporting policies file, corresponding to the exemplary reporting policies shown in FIG. 3. Among other things, the content 400 of the reporting policies file indicates the name of a viewing entity ("Institute01"), the policy ID of the reporting policies file ("0123456"), the type of test (assay) to report ("Xpert MTB/Rif"), a start date ("2011/01/01 00:00:00.0001"), and a number of tests to be reported per cycle ("5"). The content 400 of the reporting policies further indicates the authorization levels associated with the viewing entity ("Institute01"), corresponding to the categories of data that can be included in subsequent reporting. Specifically, authorization levels/categories of data entitled "Basic," "Assay," and "Result" are included in reporting; "Details" and "Support" are not; and "SystUser" can be included if authorized by a lab user. (As shown in FIGS. 3 and 4, the names of authorization levels/categories of data included in the content 400 of the reporting policies do not need to match the names indicated in reporting policies user interface 300.) As indicated previously, the reporting policies file is distributed to one or more corresponding medical devices 140. Although the file in FIG. 4 is provided in XML format, embodiments may utilize reporting policies files provided in another meta-language and/or format.

Figure 5:
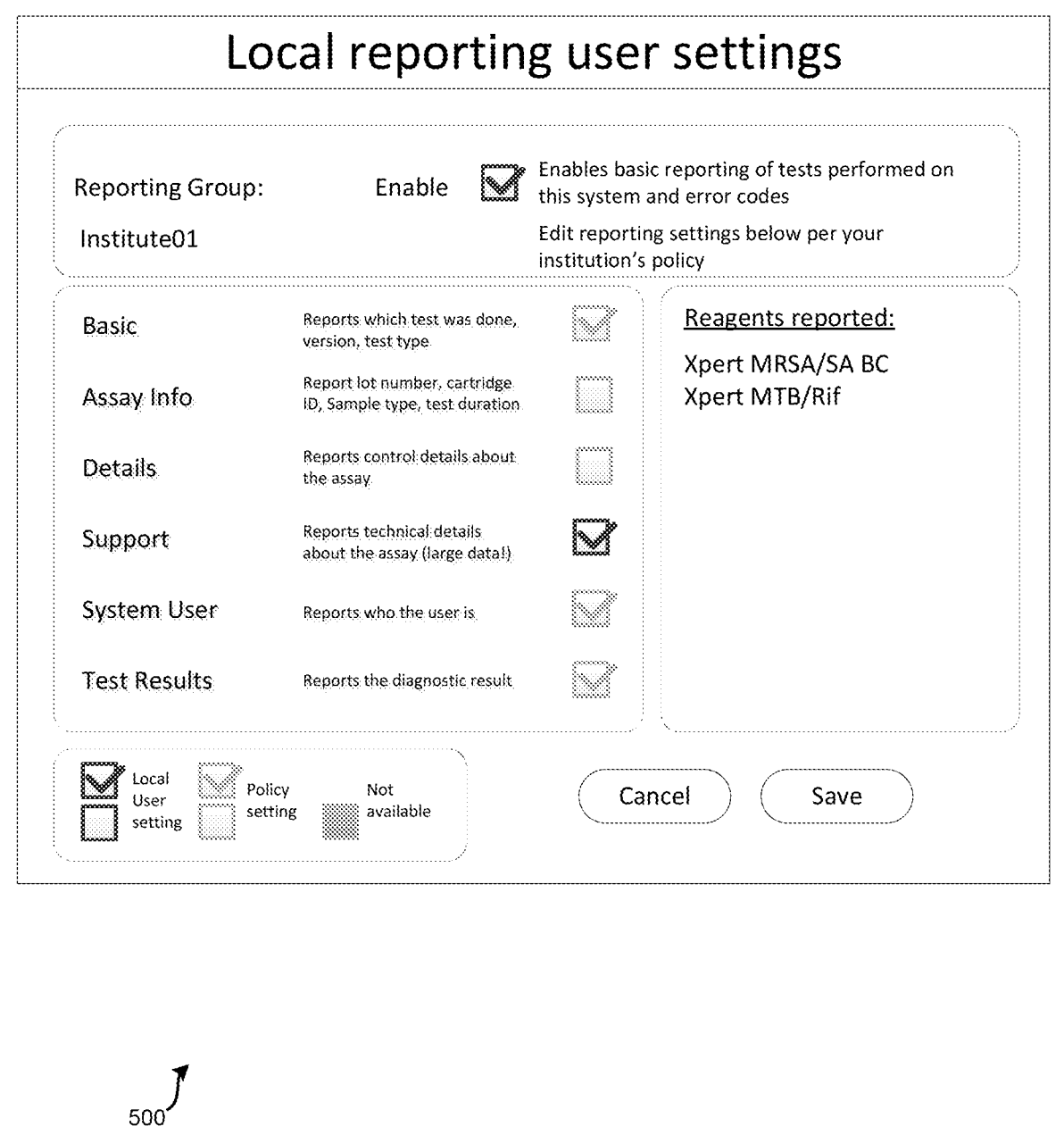

Once the reporting policies file is received by a medical device 140, the medical device can notify a lab user 290 of the receipt and enable the lab user 290 to implement the reporting policies as reporting settings on the medical device 140. FIG. 5 is an illustration of a local reporting settings user interface 500, providing an example of how a lab user can implement the reporting policies from a reporting policies file.

FIG. 5 continues the example shown in FIGS. 3 and 4, with corresponding categories of data. In this example, the local reporting settings user interface 500 indicates that certain categories of data ("Basic," "Support," "System User," and "Test Results"), are selected for reporting to the viewing entity "Institute01," while other categories of data ("Assay Info" and "Details") are not selected. Here, the local reporting settings user interface 500 implements the restrictions of the reporting policies file by enabling only one category of data, "Support," for selection (or deselection) by the lab user 290. In this example, the local reporting settings user interface 500 also allows the lab user 290 to enable basic reporting of tests and error codes, as well as save or cancel the lab user's changes made on the local reporting settings user interface 500.

Once the reporting policies are saved as reporting settings on the medical device 140, the medical device 140 can then report the test results accordingly. Referring again to FIG. 2, the reporting settings UI 210, which can display the local reporting settings user interface 500, can report selections made by the lab user 290 to the test monitor 240, which can store the corresponding reporting settings in storage 250. According to one embodiment, a resident agent subcomponent of the test monitor can periodically check the reporting settings to determine the reporting needed, query a database maintained by the testing software 220 to determine whether there are test results to be reported, and produce one or more reporting files containing the test results with the level of detail requested by corresponding reporting policy file(s). Depending on desired functionality, the test monitor 240 can then deliver the one or more reporting files to the transport agent 270 directly, or place it in storage 250 for retrieval by the transport agent 270. In some embodiments, the one or more reporting files can be placed in a particular data location (e.g., a "test results" folder), which is periodically checked by the transport agent 270. The transport agent 270 then delivers the one or more reporting files to the data center/web portal 120 for data aggregation and reporting to corresponding viewing entities.

FIG. 6 illustrates the content 600 of a reporting file, corresponding to the exemplary reporting policies shown in FIGS. 3-5. Among other things, the content 600 of the reporting file indicates the authorization levels of each viewing entity to which the results are reported in a section labeled "<Policies>", reflecting the policies included in one or more reporting policies files, and "flagging" (embedding) the test result data with authorization information. The viewing entity "Institute01," for example, is provided "Basic," "Assay," "Result," and "SystUser" authorization levels, corresponding to the selected data category types shown in FIG. 5. Additionally, a viewing entity named "WHO" is provided "Basic" and "Result" authorization levels. The data associated with each of the authorization levels is provided in the "<Test>" portion of the content 600 of the reporting file, along with additional information in the "<ID>" sub-portion regarding the medical device 140 and corresponding medical test.

Embedding the authorization information in reporting files in this manner can be advantageous for the data center/web portal 120 to perform data aggregation. Because test results are stored in the data center/web portal 120 with authorization levels for each policy, access to test results on the portal are synchronized with the authorization level of the viewing entity at all times, as authorized both by the institution administrator and by the lab user. This can allow for reliable, real-time data filtering based on the authorization type of the viewing entity. Depending on desired functionality, the data center/web portal 120 can display test results and/or aggregated test results in a variety of forms, such as lists, charts, graphs, geographic maps, and the like.

Real-time data filtering enabled by embedding authorization information in the reporting files can provide a level of accuracy and speed far beyond current reporting techniques. For example, embodiments can provide a web portal with map-based reporting that geographically indicates up-to-date test results for tuberculosis (TB), human immunodeficiency virus (HIV), sexually transmitted diseases (STDs) (e.g., *chlamydia*, gonorrhea, etc.), flu, and/or other infectious diseases. This can allow health systems, government agencies, and other entities to quickly identify specific areas of high rates of infection, or monitor viral loads and/or infection rates to predict future infection hot spots, and take appropriate action. Furthermore, because test results can be traced to particular institutions, buildings, or medical devices 140 (including mobile medical devices that can be temporarily deployed at particular locations), reporting can indicate accuracy to a higher level of detail than current techniques, which are typically limited to a city or a region. Moreover, because building- or lab-specific results can be reported, institutions such as hospitals and health-care providers can monitor test results of their own buildings and labs to ensure they comply with internal standards and/or governmental regulations. For example, reporting can indicate instances of Methicillin-resistant *Staphylococcus aureus* (MRSA), *C. difficile*, or other infectious outbreaks at certain locations and quickly respond accordingly.

Again, although the file in FIG. 6 is provided in XML format, embodiments can utilize reporting policies files provided in another meta-language and/or format. Furthermore, it will be understood that the user interfaces and files shown in FIGS. 3-6 are examples only. The techniques provided herein can be utilized in a variety of ways and extended to various embodiments in addition to those detailed herein. For example, not only can exchanges between components of the medical device be performed through files and folders as indicated previously, but they can additionally or alternatively be performed through other various means of communications between software applications, such as function calls or webservice calls.

Figure 7:
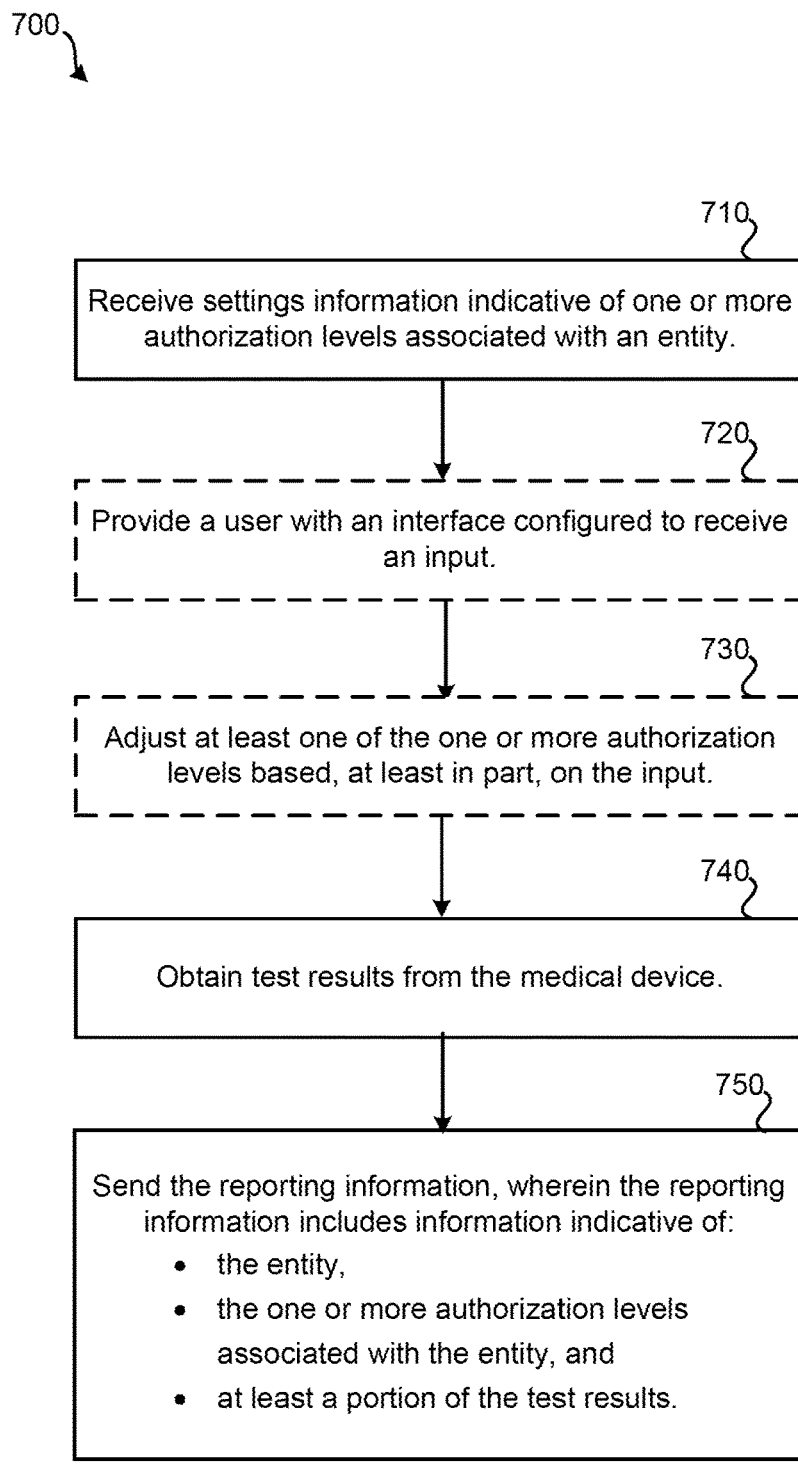
FIG. 7 is a flow diagram illustrating an exemplary computer-implemented method for processing test results of a medical device.

FIG. 7 is a flow diagram illustrating an exemplary embodiment of computer-implemented method for processing test results of a medical device 700, which can be performed, for example, by software and/or hardware of a medical device 140 and/or a computing device associated with a medical device 140. At block 710 settings information is received, the settings information indicative of one or more authorization levels associated with an entity. As discussed previously, the settings information (or policy information) can be provided in a reporting policies file, although other forms of communicating settings can be used. Authorization levels associated with an entity (e.g., a viewing entity) can include, for example, categories of data to provide for reporting to the entity. In some embodiments, particular elements of data can be included in the settings information. Any number of authorization levels may be used, depending on desired functionality.

Optionally, at blocks 720 and 730, a user can be provided with an interface configured to receive an input, and at least one of the one or more authorization levels can be adjusted based, at least in part, on the input. The interface can be, for example, a graphical user interface, such as the local reporting settings user interface 500 of FIG. 5, shown on a screen or other electrical display device communicatively coupled with a medical device. Authorization levels can be adjusted based, at least in part, on the input of a lab user, who can accept, override, or adjust certain authorization levels. Some embodiments can allow an institution administrator to determine whether to grant lab users the ability to adjust authorization levels in this manner.

At block 740, test results are obtained from the medical device. This can include obtaining test results from one component of a medical device by another component. As shown in FIG. 2, for example, the test monitor 240 obtains the test results from testing software 220, which works with the testing hardware 230 of the medical device to determine the test results. In some embodiments, test results can be obtained from a separate device.

At block 750 the reporting information is sent. The reporting information includes information indicative of the entity, which can be a serial number, model number, and/or another identifier. As discussed previously, reporting information can further be flagged with one or more authorization levels associated with the entity. As shown herein, the one or more authorization levels can include categories of data to report to viewing entities, and a single reporting file can be flagged with authorization levels for multiple viewing entities, depending on desired functionality. Additionally, the reporting information will include at least a portion of the test results for reporting to the viewing entity.

Figure 8:
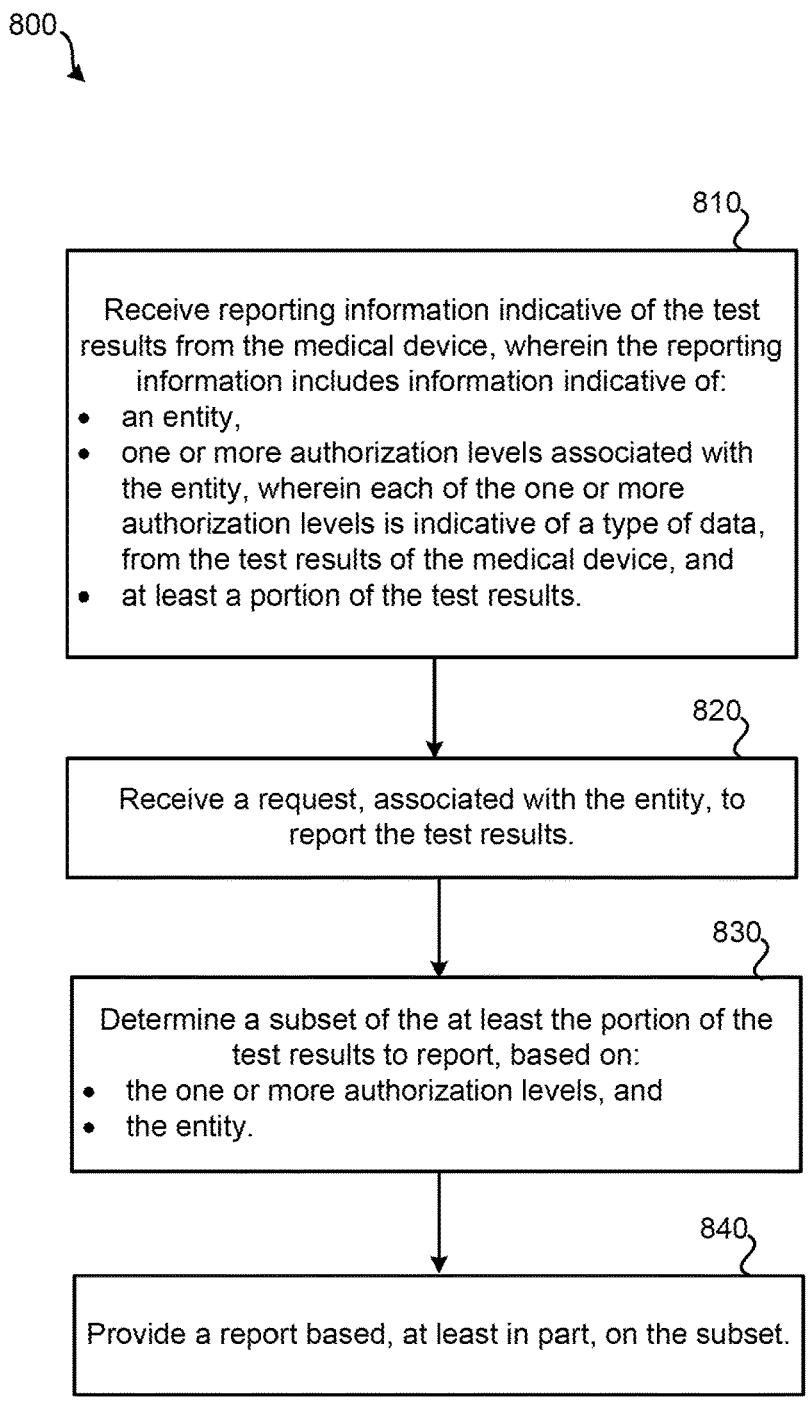
FIG. 8 is a flow diagram illustrating an exemplary process for reporting test results from a medical device that are flagged with authorization information.

FIG. 8 is a simplified flow diagram of a process 800 for reporting test results from a medical device that are flagged with authorization information. The process, which can be executed by a device or system (e.g., the data center/web portal 120 of FIGS. 1A and 1B) communicatively coupled with a medical device, can begin at block 810, where reporting information is received. The reporting information not only includes information indicative of at least a portion of the test results from the medical device, but can also include information indicating an entity (e.g., a viewing entity) and one or more authorization levels associated with the entity. As discussed herein, such authorization levels can indicate types or categories of data to report to a viewing entity.

At block 820 a request to report the test results is received. The request, which is associated with the entity (e.g., viewing entity), can be made from a user device 150 via a web portal, application, or other communication program. The requested test results can be one of several test results and/or aggregated test results to report to the entity.

At block 830, a subset of the at least the portion of the test results to report is determined. The subset is based on the one or more authorization levels and the entity. In the example shown in FIGS. 3-6, for instance, the authorization levels granted to the entity "Institute01" enable corresponding portions of the test results to be reported to the "Institute01" entity. Namely, test results corresponding to the data categories entitled "Basic," "Assay," "Result," and "SystUser" in the reporting file (see FIG. 6) can be reported. Depending on the type of report requested, some or all of this information can be provided to the "Institute01" entity. At block 840, the report is provided, based at least in part on the subset. As indicated above, the report can be displayed in a variety of forms, such as lists, charts, graphs, geographic maps, and/or the like.

It should be appreciated that the specific steps illustrated in FIGS. 7 and 8 provide examples of methods for processing and reporting test results of medical devices. Alternative embodiments may include alterations to the embodiments shown. For example, alternative embodiments may include additional steps for processing and/or aggregating data based on one or more factors such as location, test type, medical device type, results, and the like. Embodiments can also allow an entity to send several reporting policies (e.g., several files containing settings information) to one or more medical devices, in which case a "sum" of all test results collected by the reporting policies can be provided to the viewing entity. Furthermore, additional features can be added, removed, or combined depending on the particular applications. One of ordinary skill in the art would recognize many variations, modifications, and alternatives that fall within the scope of the present disclosure.

Figure 9:
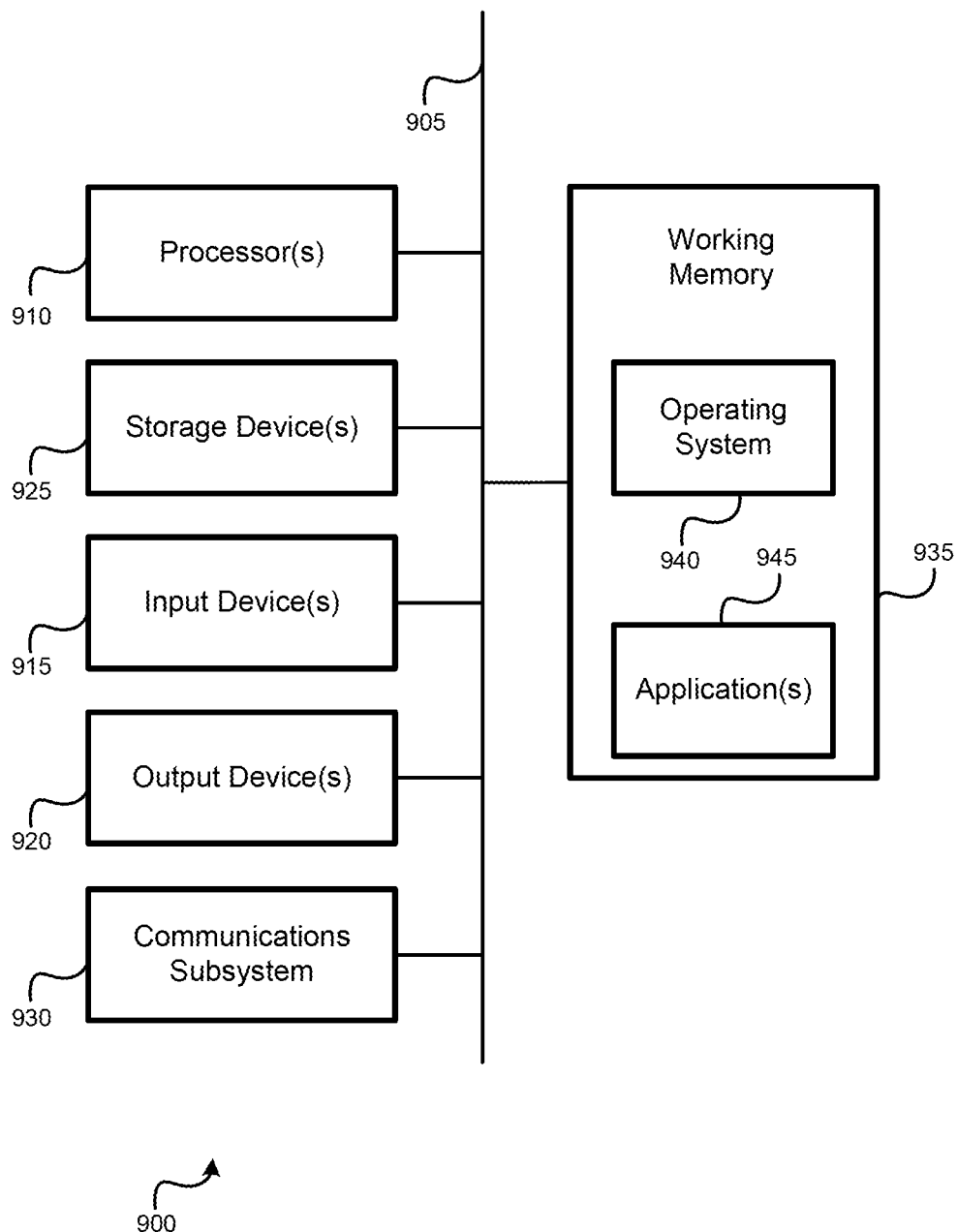
FIG. 9 is an exemplary illustration of a computer system, which may be incorporated, at least in part, into devices configured to perform some or all of the methods described herein.

FIG. 9 is an exemplary illustration of a computer system 900, which can be incorporated, at least in part, into devices and components of the distributed network 100 such the one or more medical devices 140, user devices 150, transportation platform 130, institution server 160, internal data server and/or data center/web portal 120 of FIGS. 1A and 1B. FIG. 9 provides a schematic illustration of a computer system 900 that can perform the methods provided by various embodiments of the invention. It should be noted that FIG. 9 is meant only to provide a generalized illustration of various components, any or all of which can be utilized as appropriate. FIG. 9, therefore, broadly illustrates how individual system elements can be implemented in a relatively separated or relatively more integrated manner.

The computer system 900 is shown comprising hardware elements that can be electrically coupled via a bus 905 (or may otherwise be in communication, as appropriate). The hardware elements can include a processing unit, such as processor(s) 910, which can include without limitation one or more general-purpose processors, one or more special-purpose processors (such as digital signal processing chips, graphics acceleration processors, and/or the like), and/or other processing means; one or more input devices 915, which can include without limitation a mouse, a keyboard, a camera, a microphone, a touchscreen, medical testing hardware, and/or the like; and one or more output devices 920, which can include without limitation a display device, a printer, and/or the like.

The computer system 900 can further include (and/or be in communication with) one or more non-transitory storage devices 925, which can comprise, without limitation, local and/or network accessible storage, and/or can include, without limitation, a disk drive, a drive array, an optical storage device, a solid-state storage device, such as a random access memory ("RAM"), and/or a read-only memory ("ROM"), which can be programmable, flash-updateable, and/or the like. Such storage devices can be configured to implement any appropriate data stores, including without limitation, various file systems, database structures, and/or the like.

The computer system 900 can include a communications subsystem 930, which can include without limitation a modem, a network card (wireless or wired), an infrared communication device, a wireless communication device, and/or a chipset (such as a Bluetooth™ device, an 802.11 device, a WiFi device, a WiMax device, cellular communication facilities, etc.), and/or the like. The communications subsystem 930 can include one or more input and/or output communication interfaces to permit data to be exchanged with a network (such as the data communication network(s) 110 of FIGS. 1A and 1B), other computer systems, and/or any other electrical devices described herein. Depending on the desired functionality and/or other implementation concerns, a portable electronic device (or similar device) can communicate image and/or other information via the communications subsystem 930. In many embodiments, the computer system 900 will comprise a working memory 935, which can include a RAM or ROM device, as described above.

The computer system 900 can comprise software elements, shown as being currently located within the working memory 935, including an operating system 940, device drivers, executable libraries, and/or other code, such as one or more application programs 945, which can comprise computer programs provided by various embodiments, and/or can be designed to implement methods, and/or configure systems, provided by other embodiments, as described herein. Merely by way of example, one or more procedures described with respect to the method(s) discussed above, such as those described in relation to FIGS. 7 and 8, might be implemented as code and/or instructions executable by a computer (and/or a processing unit within a computer); in an aspect, then, such code and/or instructions can be used to configure and/or adapt a general purpose computer (or other device) to perform one or more operations in accordance with the described methods.

A set of these instructions and/or code can be stored on a non-transitory computer-readable storage medium, such as the storage device(s) 925 described above. In some cases, the storage medium can be incorporated within a computer system, such as computer system 900. In other embodiments, the storage medium can be separate from a computer system (e.g., a removable medium, such as an optical disc), and/or provided in an installation package, such that the storage medium can be used to program, configure, and/or adapt a general purpose computer with the instructions/code stored thereon. These instructions can take the form of executable code, which is executable by the computer system 900 and/or can take the form of source and/or installable code, which, upon compilation and/or installation on the computer system 900 (e.g., using any of a variety of generally available compilers, installation programs, compression/decompression utilities, etc.), then takes the form of executable code.

It will be apparent to those skilled in the art that substantial variations can be made in accordance with specific requirements. For example, customized hardware can be used, and/or particular elements can be implemented in hardware, software (including portable software, such as applets, etc.), or both. Connection to other computing devices such as network input/output devices can be employed.

Some embodiments can employ a computer system (such as the computer system 900) to perform methods in accordance with various embodiments of the invention. In some embodiments, some or all of the procedures of such methods are performed by the computer system 900 in response to processor(s) 910 executing one or more sequences of one or more instructions (which can be incorporated into the operating system 940 and/or other code, such as an application program 945) contained in the working memory 935. Such instructions can be read into the working memory 935 from another computer-readable medium, such as one or more of the storage device(s) 925. Merely by way of example, execution of the sequences of instructions contained in the working memory 935 can cause the processor(s) 910 to perform one or more procedures of the methods described herein. Additionally or alternatively, portions of the methods described herein can be executed through specialized hardware.

The terms "machine-readable storage medium" and "computer-readable storage medium," as used herein, refer to any storage medium that participates in providing data that causes a machine to operate in a specific fashion. In some embodiments implemented using the computer system 900, various computer-readable media can be involved in providing instructions/code to processor(s) 910 for execution and/or can be used to store and/or carry such instructions/code. In many implementations, a computer-readable storage medium is a physical and/or tangible storage medium. Such a medium can take the form of a non-volatile media or volatile media. Non-limiting examples of non-volatile media can include, optical and/or magnetic disks, such as the storage device(s) 925. Non-limiting examples of volatile media can include, without limitation, dynamic memory, such as the working memory 935.

Non-limiting common forms of physical and/or tangible computer-readable media can include, for example, a floppy disk, a flexible disk, hard disk, magnetic tape, or any other magnetic medium, a CD-ROM, any other optical medium, a RAM, a PROM, EPROM, a FLASH-EPROM, any other memory chip or cartridge, or any other medium from which a computer can read instructions and/or code.

Various forms of computer-readable media can be involved in carrying one or more sequences of one or more instructions to the processor(s) 910 for execution. Merely by way of example, the instructions may initially be carried on a magnetic disk and/or optical disc of a remote computer. A remote computer can load the instructions into its dynamic memory and send the instructions as signals over a transmission medium to be received and/or executed by the computer system 900.

The communications subsystem 930 (and/or components thereof) generally will receive signals, and the bus 905 then can carry the signals (and/or the data, instructions, etc. carried by the signals) to the working memory 935, from which the processor(s) 910 retrieves and executes the instructions. The instructions received by the working memory 935 can optionally be stored on a non-transitory storage device 925 either before or after execution by the processor(s) 910.

The methods, systems, and devices discussed above are examples. Various configurations can omit, substitute, or add various procedures or components as appropriate. For instance, in alternative configurations, the methods can be performed in an order different from that described, and/or various stages can be added, omitted, and/or combined. Also, features described with respect to certain configurations can be combined in various other configurations. Different aspects and elements of the configurations can be combined in a similar manner. Also, technology evolves and many of the elements as described are provided as non-limiting examples and thus do not limit the scope of the disclosure or claims.

Specific details are given in the description to provide a thorough understanding of exemplary configurations (including implementations). However, configurations can be practiced without these specific details. For example, well-known circuits, processes, algorithms, structures, and techniques have been shown without unnecessary detail in order to avoid obscuring the configurations. This description provides exemplary configurations that do not limit the scope, applicability, or configurations of the claims. Rather, the preceding description of the configurations will provide those skilled in the art with an enabling description for implementing described techniques. Various changes can be made in the function and arrangement of elements without departing from the spirit or scope of the disclosure.

Also, configurations can be described as a process which is depicted as a flow diagram or block diagram. Although each can describe the operations as a sequential process, many of the operations can be performed in parallel or concurrently. Furthermore, examples of the methods can be implemented by hardware, software, firmware, middleware, microcode, hardware description languages, or any combination thereof. When implemented in software, firmware, middleware, or microcode, the program code or code segments to perform the necessary tasks can be stored in a non-transitory computer-readable medium such as a storage medium. Processors can perform the described tasks.

Terms, "and" and "or" as used herein, may include a variety of meanings that also is expected to depend at least in part upon the context in which such terms are used. Typically, "or" if used to associate a list, such as A, B, or C, is intended to mean A, B, and C, here used in the inclusive sense, as well as A, B, or C, here used in the exclusive sense. In addition, the term "one or more" as used herein may be used to describe any feature, structure, or characteristic in the singular or may be used to describe some combination of features, structures, or characteristics. However, it should be noted that this is merely an illustrative example and claimed subject matter is not limited to this example. Furthermore, the term "at least one of" if used to associate a list, such as A, B, or C, can be interpreted to mean any combination of A, B, and/or C, such as A, AB, AA, AAB, AABBCCC, etc.

Having described several exemplary configurations, various modifications, alternative constructions, and equivalents can be used without departing from the spirit of the disclosure. For example, the above elements can be components of a larger system, wherein other rules can take precedence over or otherwise modify the application of the invention. Also, a number of steps can be undertaken before, during, or after the above elements are considered. Accordingly, the above description does not bound the scope of the claims.

What is claimed is:

1. A method for processing test results of a molecular diagnostic medical device, the method comprising:
   creating an XML reporting policies file with a plurality of authorization levels, each authorization level corresponding to a type of viewing entity and being indicative of a type of data from the test results of the molecular diagnostic medical device that is viewable by the type of viewing entity, wherein the viewing entity is an individual or organization with authorization to view epidemiological data;
   loading the XML reporting policies file onto a plurality of molecular diagnostic medical devices over a distributed network, the plurality of molecular diagnostic medical devices being identified in the XML reporting policies file;
   storing information from the XML reporting policies file to a memory of the molecular diagnostic medical device;
   obtaining, by the molecular diagnostic medical device, medical test results;
   creating, in the molecular diagnostic medical device, a reporting file comprising the medical test results;
   embedding information regarding the authorization level of reports for each viewing entity from the XML reporting policies file into the reporting file, wherein:
      the medical test results are categorized into a plurality of data categories based on the plurality of authorization levels in the reporting policy for the viewing entities, each data category corresponding to a respective authorization level, and
      the reporting file identifies the viewing entities and the plurality of authorization levels of the viewing entities;
   sending, from the molecular diagnostic medical device to a data center over the distributed network, the reporting file including the medical test results, an identifier of the viewing entity, and the plurality of authorization levels of the viewing entities embedded within the reporting file;
   requesting access to the test results by a requesting entity; and
   using an authorization level in the reporting file corresponding to the requesting entity accessing to do real-time data filtering based on an authorization type to provide access to only authorized data.

2. The method of claim 1, further comprising:
   obtaining, for each viewing entity of one or more additional viewing entities, a respective reporting policies file comprising a respective reporting policy indicating one or more authorization levels of the respective viewing entity; and
   for each viewing entity of the one or more additional viewing entities, including, in the reporting file, an indication of the one or more authorization levels of the respective viewing entity.

3. The method of claim 1, further comprising receiving a user input indicative of a confirmation of one or more reporting policies of the reporting policies file, wherein saving the information from the reporting policies file is in response to receiving the confirmation of the one or more reporting policies.

4. The method of claim 1, wherein the reporting policy further indicates:
a type of medical test to include in the reporting file,
a start date to provide the reporting file, or
a number of tests reported in a certain period of time, or any combination thereof.

5. The method of claim 1, further comprising:
receiving a user input separate from the reporting policies file, the user input indicative of a label, a type, and an authorization level associated with a new data field; and
including, in the reporting file, the new data field.

6. The method of claim 5, further comprising adjusting one or more authorization levels of the viewing entity based on the user input.

7. The method of claim 1, wherein obtaining the reporting policies file at the medical device comprises scanning a particular data location for the reporting policies file.

8. The method of claim 1, wherein sending the reporting file comprises storing the reporting file at a particular data location for transmittal.

9. The method of claim 1, wherein the reporting file further includes an identifier of the medical device.

10. The method of claim 1, wherein the reporting file further includes a cartridge identifier of an assay cartridge related to the medical test results.

11. The method of claim 10, wherein the data center aggregates data in the reporting file received from the medical device with data in reporting files received from other medical devices to generate aggregated test results for the viewing entity based on reporting policies information contained in each of the reporting files.

12. The method of claim 1, wherein the reporting file being sent is a markup language file containing a reporting policies section and a test results section.

13. A molecular diagnostic medical device for processing test results, the molecular diagnostic medical device comprising:
a memory;
a communication interface to a distributed network; and
a processing unit communicatively coupled with the memory and the communication interface, wherein the processing unit is configured to:
receive an XML reporting policies file with one or more authorization levels, each authorization level corresponding to a type of viewing entity and being indicative of a type of data from the test results of the molecular diagnostic medical device that is viewable by the type of viewing entity, wherein the viewing entity is an individual or organization with authorization to view epidemiological data, wherein the molecular diagnostic medical device is identified in the XML reporting policies file;
cause information from the XML reporting policies file to be stored in the memory;
obtain medical test results;
create a reporting file comprising the medical test results;
embed information regarding the authorization level of reports for each viewing entity from the reporting policies file into the reporting file, wherein:
the medical test results are categorized into a plurality of data categories based on the plurality of authorization levels in the reporting policy for the viewing entities, each data category corresponding to a respective authorization level, and
the reporting file identifies the viewing entity and the one or more authorization levels of the viewing entity; and
send, via the communication interface to a data center over a distributed network, the reporting file including the medical test results, an identifier of the viewing entity, and the one or more authorization levels of the viewing entity embedded within the reporting file, enabling the data center to receive a request for access to the test results by a requesting entity, and to use an authorization level in the reporting file corresponding to the requesting entity to do real-time data filtering based on an authorization type to provide access to only authorized data.

14. The molecular diagnostic medical device of claim 13, wherein the processing unit is further configured to:
obtain, for each viewing entity of one or more additional viewing entities, a respective reporting policies file comprising a respective reporting policy indicating one or more authorization levels of the respective viewing entity; and
for each viewing entity of the one or more additional viewing entities, include, in the reporting file, an indication of the one or more authorization levels of the respective viewing entity.

15. The molecular diagnostic medical device of claim 13, further comprising an input device, wherein:
the processing unit is further configured to receive, via the input device a user input indicative of a confirmation of one or more reporting policies of the reporting policies file; and
the processing unit is configured to save the information from the reporting policies file in response to receiving the confirmation of the one or more reporting policies.

16. The molecular diagnostic medical device of claim 13, further comprising an input device, wherein the processing unit is further configured to:
receive, from the input device, a user input separate from the reporting policies file, the user input indicative of a label, a type, and an authorization level associated with a new data field; and
include, in the reporting file, the new data field.

17. The molecular diagnostic medical device of claim 16, wherein the processing unit is further configured to adjust one or more authorization levels of the viewing entity based on the user input.

18. The molecular diagnostic medical device of claim 13, wherein, obtaining the reporting policies file comprises scanning a particular data location for the reporting policies file.

19. The molecular diagnostic medical device of claim 13, wherein sending the reporting file comprises storing the reporting file at a particular data location for transmittal.

20. The molecular diagnostic medical device of claim 13, wherein the processing unit is further configured to include, in the reporting file, an identifier of the medical device.

* * * * *